United States Patent [19]

Leonardo

[11] Patent Number: 4,635,587

[45] Date of Patent: Jan. 13, 1987

[54] METHOD AND APPARATUS FOR DETECTING STANDING HEAT IN CATTLE

[75] Inventor: John Leonardo, El Nido, Calif.

[73] Assignee: Cowtronics, Inc., Merced, Calif.

[21] Appl. No.: 741,838

[22] Filed: Jun. 6, 1985

[51] Int. Cl.⁴ ........ A01K 29/00; A61B 10/00; G08B 23/00

[52] U.S. Cl. ........ 119/1; 128/738; 340/573

[58] Field of Search ........ 119/1; 340/573; 128/738, 774, 775

[56] References Cited

U.S. PATENT DOCUMENTS

| | | | |
|---|---|---|---|
| 3,076,431 | 2/1963 | Rule et al. | 119/1 |
| 3,158,134 | 11/1964 | Larson | 119/1 |
| 3,205,857 | 12/1965 | Larson | 119/1 |
| 3,297,020 | 1/1967 | Mathiesen | 119/1 X |
| 3,533,095 | 10/1970 | Collins | 119/1 X |
| 3,844,273 | 10/1974 | Polson | 119/1 X |
| 3,948,249 | 4/1976 | Ambrosini | 119/1 X |
| 4,055,839 | 10/1977 | Skeggs | 119/1 X |
| 4,206,766 | 6/1980 | Bielka | 119/1 X |
| 4,239,018 | 12/1980 | Griffin et al. | 119/1 |
| 4,247,758 | 1/1981 | Rodrian | 119/1 X |
| 4,411,274 | 10/1983 | Wright | 128/738 |
| 4,455,610 | 6/1984 | Rodrian | 119/1 X |

*Primary Examiner*—Carlton R. Croyle
*Assistant Examiner*—Paul F. Neils
*Attorney, Agent, or Firm*—Harris Zimmerman; Howard Cohen

[57] ABSTRACT

A method and apparatus for detecting standing heat in cattle includes an electronic timer module connected to a membrane switch. The module includes a digital time readout display, as well as audible and visible indicators. A saddle-like sleeve includes a transparent pocket having a sealable opening adapted to receive the timer module and membrane switch therein. The sleeve is adapted to be adhered to the base of the tail of a cow. The membrane switch is adapted to be actuated by the weight of other cows attempting to mount the cow when in heat. The switch actuates the timer, and also actuates intermittent operation of the audible and visible indicators to warn the cattle owner that the cow is in heat, and also to indicate exactly when the cow came into heat.

12 Claims, 4 Drawing Figures

METHOD AND APPARATUS FOR DETECTING STANDING HEAT IN CATTLE

BACKGROUND OF THE INVENTION

The following United States patents represent the closest known prior art, U.S. Pat. Nos.: 3,076,431; 3,158,133; 3,158,134; 3,205,857; 3,297,020; 3,844,273; 3,948,249; 4,239,018; 4,247,758.

Since the advent of artificial insemination techniques, it has been possible to breed cattle to optimize characteristics such as size, milk productivity, disease resistance, and the like. However, although artificial insemination no longer requires the presence of the breeding bull at the time of insemination, it still requires that the farmer or rancher determine the exact time of estrus of a cow, so that the insemination will fertilize the cow. The accurate detection estrus, or standing heat in cattle, is a problem long recognized but unsolved in the prior art.

A cow comes into heat approximately every 21 days, and then remains in heat for approximately 10 to 12 hours. The cow then ovulates approximately 14 hours after going out of heat. The time of ovulation is the optimum time for artificial insemination. If insemination is successful, the cow will be pregnant for 280 days. After calving, the ideal situation from the farmers standpoint is to reimpregnate the cow within 45 to 60 days after calving.

However, if it is not known when the cow first entered heat, the timing of the artificial insemination must be approximate, and a significant number of inseminations will fail to produce pregnancy. The farmer must then wait for the next estrus period to again attempt insemination. It is reliably estimated that it cost a dairyman three dollars per day per cow if the cow is not pregnant when it could be pregnant. In an average size dairy herd of 400 cows, with an average calving interval of 14 months, accurate determination of standing heat could lower the calving interval to an average of 11.5 months. This savings of 45 days in the pregnancy cycle, multiplied by three dollars per day and by 400 cattle, can result in a net savings of $54,000 per year. Thus it is clear that the accurate determination of estrus onset in cattle is extremely important to dairymen, as well as other cattle breeders.

One type of device known in the prior art for detecting standing heat employs a dye or dye forming chemicals disposed in a frangible pack and secured to the base of the tail of each cow in a herd. With the onset of estrus in any cow, the other cows will try to mount the one in heat, breaking the frangible pack and spreading the dye over the animal sufficiently to warn the cattleman that the cow has entered heat. However, if several cows enter heat on the same day, or if precipitation should wash away the dye, it is difficult to determine which cow is in heat. Furthermore, it cannot be determined to within 12-24 hours when estrus has begun, so that the timing of insemination involves too much guesswork and not enough certainty.

Another approach known in the prior art employs a temperature sensor placed in the vagina of the cow, and includes a radio transmitter which emits a signal when the internal temperature rises. This temperature gain may indicate onset of estrus, or may also indicate a fever due to bovine illness. Also, experience has shown that many of these devices are lost by being expelled during urination by the cow.

Other prior art attempts to detect estrus involve a radio transmitter strapped to the leg of each cow and coupled to a pedometer. The theory is that a cow entering heat will be more restless and will take more steps per day than a cow not in heat. The radio transmitter will emit a signal indicative of the number of steps and apprise the rancher each day. However, other factors may determine the number of steps per day, such as changes in grazing habits, the presence of other animals or humans, and the like.

A significant failing of all of these methods and apparatus, in addition to the shortcomings noted already, is that they do not determine the exact time of onset of estrus, and thus cannot provide the cattle owner with accurate information for optimal timing of the artificial insemination.

SUMMARY OF THE PRESENT INVENTION

The present invention generally comprises a method and apparatus for accurately determining the time of onset of estrus in a cow, and for warning the cattle owner that the cow is in heat. Thus the timing of artificial insemination may be accurately determined to maximize the chance of impregnating the cow.

The method and apparatus for detecting standing heat in cattle includes an electronic timer module connected to a membrane switch. The module includes a digital time readout display, as well as audible and visible indicators. A saddle-like sleeve is also provided, and includes a transparent pocket having a sealable opening adapted to receive the timer module and membrane switch therein. The sleeve is adapted to be adhered to the base of the tail of a cow, with the membrane switch disposed adjacent to the spine of the cow. The membrane switch is thus positioned to be actuated by the weight of other cows attempting to mount the cow when in heat. The switch actuates the timer, and also actuates intermittent operation of the audible and visible indicators to warn the cattle owner that the cow is in heat. The timer provides a count up function, so that the digital readout provides an accurate indication of the elapsed time from the onset of estrus. This information permits an educated determination of the proper time for insemination.

DESCRIPTION OF THE PREFERRED EMBODIMENT

The present invention generally comprises a method and apparatus for determining that a cow is in heat, and also for determining the time of onset of estrus of the cow with relatively high accuracy.

Figure 4:
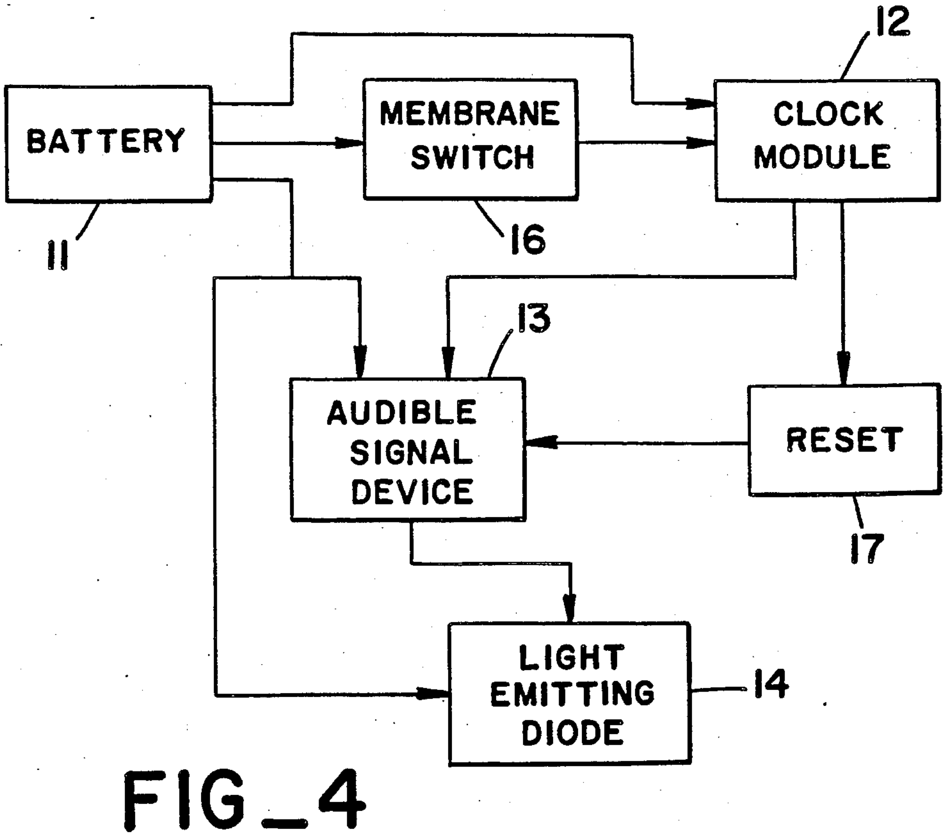
FIG. 4 is a block diagram representation of the circuitry of the electronic module of the present invention.

With regard to FIG. 4, the electronic circuitry of the present invention includes a battery 11 connected to power a clock module 12, such as a digital timer module known in the prior art. The battery 11 is also connected to drive an audible signalling device 13 and visible signalling device 14, such as a light emitting diode. A membrane or tape switch 16 is connected between the battery and the clock module 12, and is adapted to actuate the clock module, as will be explained in the following description. The membrane switch 16 is also connected through the clock module to actuate the audible and visible signalling devices 13 and 14, respectively. The clock module 12 is configured as a count up timer to count elapsed time after actuation by the switch 16. A reset button 17 is also provided to reset the timer contents to zero, so that the device may be reused many times.

In the preferred embodiment the clock module 12 comprises a customized gate array realized in a CMOS integrated circuit and produced by Accusplit, Inc, San Jose Calif. The membrane switch 16 comprises a laminated assembly of polyester material and conductive carbon ink, and is provided by the Xymox Division of the W.H. Brady Co., Milwaukee, Wis. It may be noted that other similar devices known in the art could be used by anyone having ordinary skill in the art.

Figure 1:
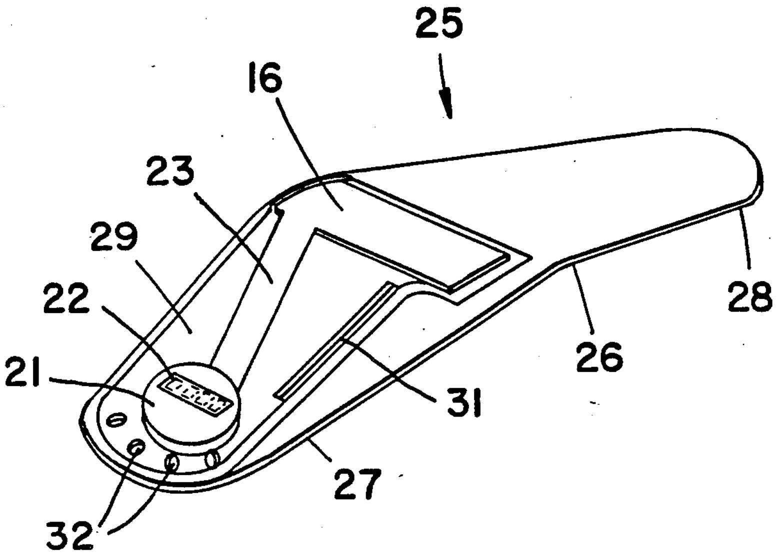
FIG. 1 is a perspective view of the sleeve and electronic module assembly of the present invention.

With regard to FIG. 1, the battery 11, clock module 12, signalling devices 13 and 14, and the reset button 17 are all secured in a small modular housing 21. The housing 21 is generally disc-like in configuration, and includes a digital time display 22 on the upper end face thereof. The membrane switch 16 is joined to the modular housing 21 by means of a flexible flat cable connector 23, or the like.

A salient feature of the present invention is the provision of a sleeve 25 which is adapted to be secured to a cow. The sleeve is formed of flexible, durable plastic material, and includes a medial portion 26 and a pair of arms 27 and 28 extending therefrom in opposed, bilateral fashion. The sleeve includes a closed pocket 29 formed of transparent, flexible plastic material and extending from the medial portion 26 to the distal extent of the arm 27. The pocket includes a sealable opening 31 extending partially along the length of the arm 27. The opening is provided with a resealable fastener, such as a linear tongue and groove snap-acting seal, a hook and loop closure, or the like. The pocket 29 is dimensioned to receive the membrane switch 16 in an orientation generally transverse to the extent of the arms 27 and 28, with the housing 21 disposed in the distal end portion of the pocket. In the distal end portion of the pocket a plurality of vent holes 32 are formed to prevent moisture accumulation within the pocket, and to release any air pressure buildup within the pocket. More importantly, the vents 32 facilitate the transmission of the audible warning signal from the device 13 to the exterior of the pocket 29.

Figure 2:
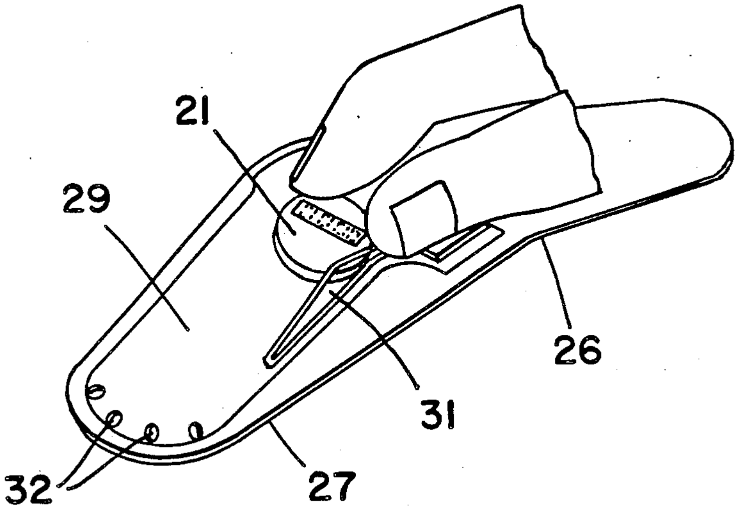
FIG. 2 is a partial perspective view of the sleeve of the present invention, showing the step of manual insertion of the electronic module into the sleeve.

The modular housing 21, the switch 16, and the connector 23 therebetween may be inserted in and removed from the pocket 29 by means of the opening 31. As shown in FIG. 2, the housing and switch assembly easily may be inserted through the opening 31 and arranged within the pocket 29 in the configuration of FIG. 1. The flexiblity of the membrane switch and the connector 23 aid in arranging the components in the proper placement.

Figure 3:
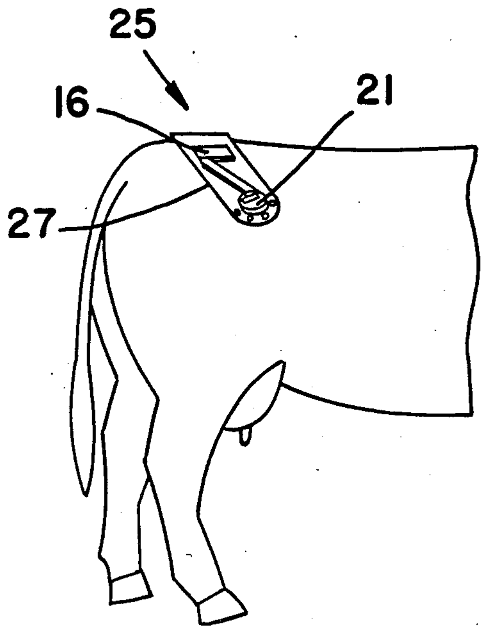
FIG. 3 is a perspective view showing the placement of the assembly of FIG. 1 on a cow.

To employ the apparatus of the present invention, the module 21, switch 16, and connector ribbon 23 are inserted into the pocket 29 of a sleeve 25, and the opening 31 is resealed. As shown in FIG. 3, the sleeve 25 is then secured to a cow with suitable adhesive. The sleeve 25 is disposed with the medial portion 26 extending over the spine of the cow directly adjacent to the base of the tail, with the arms 27 and 28 extending laterally therefrom. It should be noted that the membrane switch 16 is thus disposed directly adjacent to the rear spinal portion of the cow.

With the onset of estrus in the cow, the common behavioral trait of other cows is to attempt to mount the cow in heat. As soon as the cow is mounted the first time, the placement of the switch 16 assures that the switch will be actuated, and the clock module 12 will be activated thereby. In addition, the audible and visible signalling devices 13 and 14 will also be activated intermittently by the clock module. When the herd is next surveyed by the rancher or owner, i.e., at the next milking session, the warning signals from the devices 13 and 14 will alert the rancher to the fact that the cow is in heat. The rancher can then read the timer display 22 and ascertain how many hours have elapsed since the cow was first mounted, yielding an accurate determination of the time of onset of estrus. The rancher may then make an intelligent and informed decision as to the proper time for insemination of the cow. The clock module may also be reset to zero to deactivate the warning devices.

After insemination, when the cow has been diagnosed as pregnant, the module 21 and switch 16 may be removed from the pocket 29 of the sleeve 25 secured to the cow, and reinserted in another sleeve 25. The new assembly is then ready to be adhered to another cow for further use.

I claim:

1. A self-contained apparatus for detecting the onset of estrus in cattle, including;

a pressure responsive switch disposed to be actuated by mounting of the cow, timer means connected directly to said switch means for activation thereby in count up fashion, digital readout means connected to said timer means and disposed to display the elapsed time after mounting of the cow, audible and visible signaling means connected directly to said timer means to emit a warning signal in response to activation of said timer means, means for securing said pressure responsive switch, said time means, said readou means, and said signaling means together in closely adjacent fashion to the base of the tail of a cow; said means for securing including means for displaying said elapsed time directly from the apparatus secured to the cow, and said means for securing further including means for emitting said audible and visible warning signals directly from the apparatus secured to the cow.

2. The apparatus of claim 1, wherein said pressure responsive switch includes a flexible membrane switch.

3. The apparatus of claim 1, further including a modular housing, said timer means, said readout means, and said signalling means being secured in said modular housing.

4. The apparatus of claim 1, wherein said means for securing includes sleeve means for securing and supporting said switch means, said timer means, and said signaling means on the cow.

5. The apparatus of claim 4, wherein said sleeve means includes a flexible base member adapted to be adhered to the cow adjacent to the base of the tail thereof.

6. The apparatus of claim 5, further including a sealable pocket joined to said base member and adapted to retain said switch means, said timer means, and said signalling means.

7. The apparatus of claim 6, wherein said base member includes a medial portion and a pair of arms extending therefrom in laterally opposed fashion, said medial portion being adapted to be secured over the rear spinal portion of the cow with said arms extending laterally therefrom.

8. The apparatus of claim 7, wherein said pocket extends from said medial portion to the distal end portion of one of said arms.

9. The apparatus of claim 8, wherein said pocket is formed of transparent plastic material to facilitate visualization of said readout means and said signalling means.

10. An apparatus for detecting the onset of estrus in a cow, comprising;

a pressure responsive switch means disposed to be actuated by mounting of the cow, timer means connected to said switch means for activation thereby in count up fashion, readout means connected to said timer means and disposed to display the elapsed time after mounting of the cow, signaling means connected to said timer means to emit a warning signal in response to activation of said timer means, sleeve means for securing and supporting said switch means, said timer means, and said signaling means on the cow, said sleeve means including a flexible base member adapted to be adhered to the cow adjacent to the base of the tail thereof, a sealable pocket joined to said base member and adapted to retain said switch means, said timer means, and said signaling means, said base member including a medial portion and a pair of arms extending therefrom in laterally opposed fashion, said medial portion being adapted to be secured over the rear spinal portion of the cow with said arms extending laterally therefrom, said pocket extending from said medial portion to the distal end portion of one of said arms, said pocket being formed of transparent plastic material to facilitate visualization of said readout means and said signaling means, and a plurality of vent holes in said pocket to facilitate broadcast of audible signals from said signaling means.

11. An apparatus for detecting the onset of estrus in a cow, comprising;

a pressure responsive switch means disposed to be actuated by mounting of the cow, timer means connected to said switch means for activation thereby in count up fashion, readout means connected to said timer means and disposed to display the elapsed time after mounting of the cow, signaling means connected to said timer means to emit a warning signal in response to activation of said timer means, sleeve means for securing and supporting said switch means, said timer means, and said signaling means on the cow, said sleeve means including a flexible base member adapted to be adhered to the cow adjacent to the base of the tail thereof, a sealable pocket joined to said base member and adapted to retain said switch means, said timer means, and said signaling means, said base member including a medial portion and a pair of arms extending therefrom in laterally opposed fashion, said medial portion being adapted to be secured over the rear spinal portion of the cow with said arms extending laterally therefrom, said pocket extending from said medial portion to the distal end portion of one of said arms, said pocket being formed of transparent plastic material to facilitate visualization of said readout means and said signaling means, and a resealable opening in said pocket to facilitate removal and replacement of said timer means, said readout means, said switch means, and said signaling means.

12. A method for determining the onset and time of onset of estrus in a cow, comprising the steps of:

providing a timer module having a count up timer, digital time display, and audible and visible local signaling devices, providing a membrane switch connected to actuate said timer module, securing said membrane switch adjacent to the base of the tail of a cow, with the timer module secured directly adjacent thereto, said membrane switch being disposed to be actuated by mounting of the cow by other cows in response to onset of estrus, said membrane switch connected to activate said timer module to display elapsed time after initial mounting and to activate said local signaling device to emit said audible and visible signals directly from the animal to warn of onset of estrus in the cow.

* * * * *